US011389287B2

(12) United States Patent
Gettman

(10) Patent No.: US 11,389,287 B2
(45) Date of Patent: Jul. 19, 2022

(54) METHODS AND MATERIALS FOR TREATING URINARY CALCULI

(71) Applicant: Mayo Foundation for Medical Education and Research, Rochester, MN (US)

(72) Inventor: Matthew T. Gettman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 196 days.

(21) Appl. No.: 16/612,929

(22) PCT Filed: May 18, 2018

(86) PCT No.: PCT/US2018/033308
§ 371 (c)(1),
(2) Date: Nov. 12, 2019

(87) PCT Pub. No.: WO2018/213659
PCT Pub. Date: Nov. 22, 2018

(65) Prior Publication Data
US 2020/0163749 A1    May 28, 2020

Related U.S. Application Data

(60) Provisional application No. 62/508,894, filed on May 19, 2017.

(51) Int. Cl.
*A61F 2/04*        (2013.01)
*A61B 17/22*       (2006.01)
*A61M 27/00*       (2006.01)

(52) U.S. Cl.
CPC ........ *A61F 2/042* (2013.01); *A61B 17/22012* (2013.01); *A61M 27/002* (2013.01); *A61F 2002/047* (2013.01); *A61F 2002/048* (2013.01); *A61F 2250/0067* (2013.01); *A61F 2250/0098* (2013.01)

(58) Field of Classification Search
CPC ......... A61F 2/07; A61F 2/042; A61M 27/008; A61L 2430/22
USPC .......................................... 623/23.64–23.68
See application file for complete search history.

(56) References Cited

U.S. PATENT DOCUMENTS

| | | |
|---|---|---|
| 5,383,866 A | 1/1995 | Chang |
| 6,364,868 B1 | 4/2002 | Ikeguchi |
| 6,395,021 B1 | 5/2002 | Hart et al. |
| 7,044,981 B2 | 5/2006 | Liu et al. |

(Continued)

FOREIGN PATENT DOCUMENTS

| | | |
|---|---|---|
| EP | 2749310 | 7/2014 |
| WO | WO 00/66032 | 11/2000 |

OTHER PUBLICATIONS

Extended European Search Report in European Application No. 18801853.5 dated Feb. 18, 2020, 7 pages.

(Continued)

*Primary Examiner* — Suzette J Gherbi
(74) *Attorney, Agent, or Firm* — Fish & Richardson P.C.

(57) ABSTRACT

This document relates to methods and materials for treating urinary calculi. For example, ureteral orifice devices and methods for using ureteral orifice devices to treat urinary calculi present within a mammal (e.g., a human) are provided.

20 Claims, 13 Drawing Sheets

(56) References Cited

U.S. PATENT DOCUMENTS

| | | | |
|---|---|---|---|
| 7,674,283 B2 | 3/2010 | Mitchell et al. | |
| 7,862,552 B2* | 1/2011 | McIntyre | A61L 31/16 604/891.1 |
| 8,088,170 B2 | 1/2012 | Whitmore, III | |
| 8,221,505 B2* | 7/2012 | Skerven | A61F 2/2476 623/23.68 |
| 8,337,485 B2* | 12/2012 | Ludlow | A61L 27/18 604/544 |
| 8,343,170 B2 | 1/2013 | Massicotte et al. | |
| 9,192,460 B2* | 11/2015 | Gandhi | A61F 2/94 |
| 2002/0062148 A1 | 5/2002 | Hart | |
| 2004/0143209 A1 | 7/2004 | Liu et al. | |
| 2004/0199262 A1* | 10/2004 | Dua | A61F 2/04 623/23.7 |
| 2005/0149201 A1* | 7/2005 | McWeeney | A61M 27/008 623/23.68 |
| 2005/0240141 A1 | 10/2005 | Aliski et al. | |
| 2005/0246038 A1* | 11/2005 | O'Keefe | A61M 27/008 623/23.64 |
| 2008/0177276 A1 | 7/2008 | Teague et al. | |
| 2008/0208314 A1* | 8/2008 | Skerven | A61F 2/2476 623/1.15 |
| 2008/0234659 A1 | 9/2008 | Cheng et al. | |
| 2009/0143713 A1 | 6/2009 | Van Dam et al. | |
| 2009/0287193 A1 | 11/2009 | Desai et al. | |
| 2010/0241240 A1* | 9/2010 | Willard | A61M 27/008 623/23.66 |
| 2012/0296257 A1* | 11/2012 | Van Dam | A61B 17/11 604/9 |
| 2014/0114432 A1* | 4/2014 | Shalon | A61F 2/04 623/23.65 |
| 2014/0188247 A1* | 7/2014 | Gandhi | A61F 2/04 623/23.66 |
| 2014/0188248 A1* | 7/2014 | Gandhi | A61L 31/16 623/23.66 |
| 2014/0214175 A1 | 7/2014 | Barron et al. | |
| 2015/0005893 A1* | 1/2015 | Harrah | A61L 31/148 623/23.7 |
| 2017/0079818 A1* | 3/2017 | Pendleton | A61M 27/008 |
| 2017/0128639 A1 | 5/2017 | Erbey, II et al. | |
| 2018/0071074 A1* | 3/2018 | Ludlow | A61L 27/18 |
| 2019/0374329 A1* | 12/2019 | Forell | A61F 2/0022 |

OTHER PUBLICATIONS

International Preliminary Report on Patentability International Application No. PCT/US2018/033308 dated Nov. 28, 2019, 8 pages.
International Search Report & Written Opinion in International Application No. PCT/US2018/033308 dated Aug. 10, 2018, 15 pages.

* cited by examiner

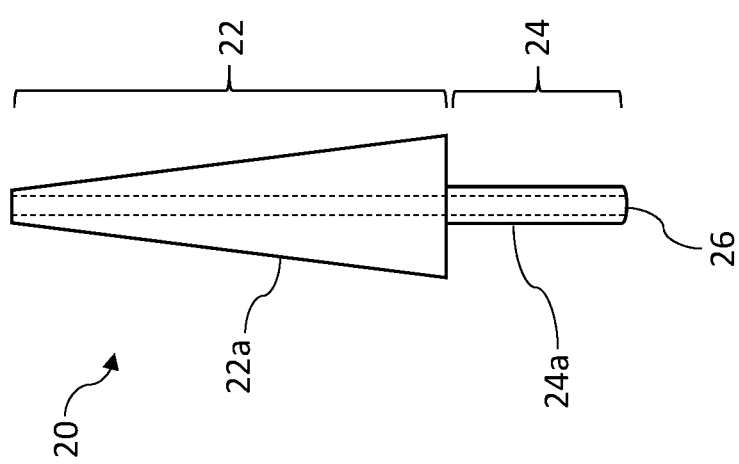

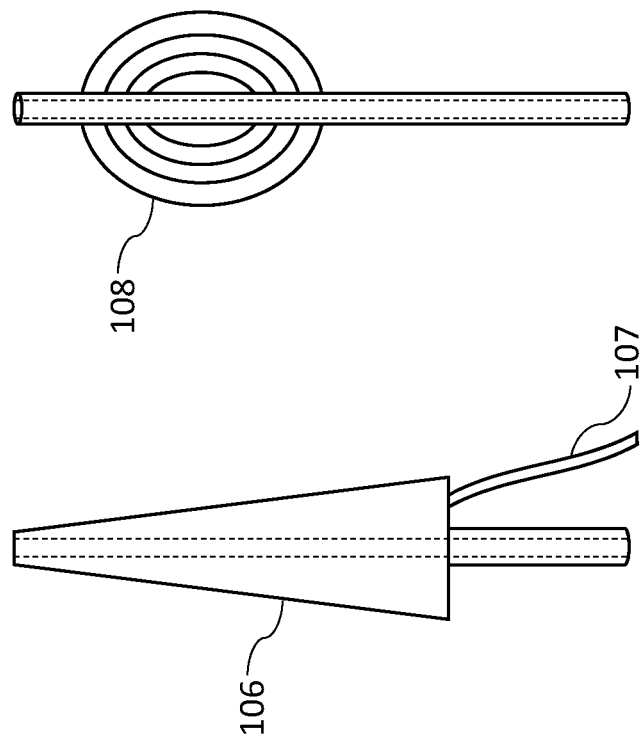
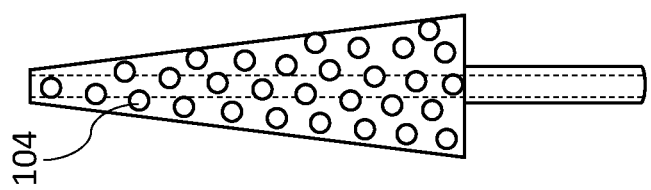
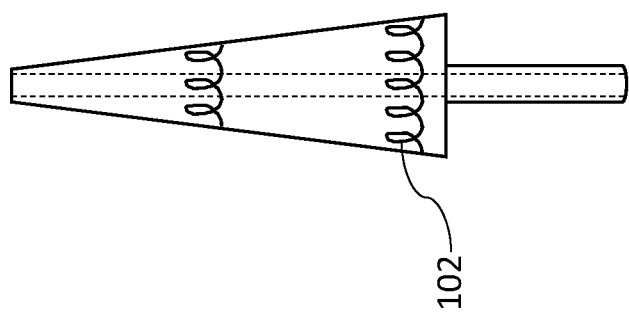
FIG. 4A  FIG. 4B  FIG. 4C  FIG. 4D

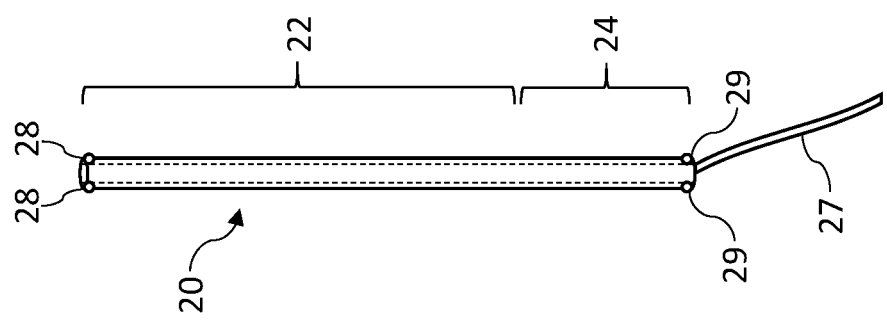

METHODS AND MATERIALS FOR TREATING URINARY CALCULI

CROSS-REFERENCE TO RELATED APPLICATIONS

This application is a National Stage application under 35 U.S.C. § 371 of International Application No. PCT/US2018/033308, having an International Filing Date of May 18, 2018, which claims priority to U.S. Application Ser. No. 62/508,894, filed on May 19, 2017. The disclosures of the prior applications are considered part of the disclosure of this application, and are incorporated in their entirety into this application.

BACKGROUND

1. Technical Field

This document relates to methods and materials for treating urinary calculi. For example, this document relates to ureteral orifice devices and methods for using ureteral orifice devices to treat urinary calculi present within a mammal (e.g., a human).

2. Background Information

Urinary calculi are a very common problem that annually afflicts millions of people worldwide. Urinary calculi can be associated with significant pain, hematuria, or obstruction. Some urinary calculi can be asymptomatic, but also require treatment if they are associated with obstruction or underlying urinary infections. When urinary calculi are untreated, they can lead to loss of renal function. Some urinary calculi can pass spontaneously from the kidney to the ureter, yet passage is often associated with pain because the size of the ureter becomes progressively smaller as it gets closer to the bladder and presence of a kidney stone can incite a pro-inflammatory, hyperperistaltic response that makes spontaneous stone passage more difficult.

The ureter is a tube that contains smooth muscle. In the normal state, urine is propelled from the kidney to the bladder by hydrostatic peristalsis of the ureter. In the normal state, the ureter is funnel shaped with a diameter of about 5-8 mm in the proximal region and about 1-2 mm at the ureteral orifice. In situations of ureteral obstruction (that are at least seen partially with ureteral stones), the region of the ureter at least proximally can increase in diameter to 8 mm or larger. Dilation of the ureter is a fundamental step that is required for spontaneous stone passage. Many stones may spontaneously pass from the kidney to the bladder. This natural process is related to the diameter of the kidney stone and the position of the stone in the ureter when the patient becomes symptomatic. For patients with stones less than 4 mm in diameter that present with symptoms in the distal ureter, about 80 percent may spontaneously pass. On the other hand, stones greater than about 8 mm in size that present at the level of the kidney have a less than 20 percent chance of passage.

SUMMARY

This document provides methods and materials for treating urinary calculi. For example, this document provides ureteral orifice devices and methods for using ureteral orifice devices to treat urinary calculi present within a mammal (e.g., a human). In some cases, the materials and methods provided herein can be used to facilitate the spontaneous passage of urinary calculi. In some cases, the methods and materials provided herein can be used to prepare a ureteral orifice for one or more later invasive or non-invasive stone removal procedures (e.g., an endoscopic procedure such as a cystoscopic, ureteroscopic, or nephroscopic procedure or a shockwave lithotripsy procedure). In some cases, the methods and materials provided herein can be used as a means to manage optimal ureteral drainage, decrease ureteral peristalsis, decrease or manage inflammation, and increase patient comfort after an invasive or non-invasive stone procedure.

As described herein, ureteral orifice devices provided herein can be used to make urinary calculi management easier, for example, by causing urinary calculi to pass and/or by preparing a ureteral orifice for a later stone removal procedure (e.g., a later invasive stone removal procedure). Without being limited to any particular mode of action, the ureteral orifice devices provided herein can promote dilation of a ureter and/or create a lower inflammatory state of a ureter within the mammal (e.g., human). For example, a ureteral orifice device provided herein can be placed at a ureteral orifice to cause gradual ambulatory dilation and/or decrease inflammation while at the same time maintaining urinary drainage. In general, a ureteral orifice device provided herein can include a luminal contact zone designed to contact the inner luminal wall of a ureter and a manipulation zone designed to extend from a ureteral orifice into the bladder. A ureteral orifice device provided herein also can define a channel that allows urine to flow from a kidney to the bladder through the device when implanted at a ureteral orifice. In some cases, implanting a ureteral orifice device provided herein into a ureteral orifice as described herein can partially impede urine flow compared to its pre-implantation urine flow rate. Without being limited to any particular mode of action, partially (approximately 20-50 percent) reducing urine flow rates compared to pre-implantation urine flow rate can allow urine flow under conditions that promote dilation of a ureter and other physiologic effects more proximally that augment the ability of the mammal to spontaneously pass the stone and/or provide the preparatory benefit for the stone removal procedure or provide the optimal post-procedural temporary ureteral state to provide drainage, manage inflammation, manage ureteral peristalsis, and thereby optimize patient comfort. In some cases, once sufficient dilation of the ureter occurs, index urinary calculi (e.g., kidney stone) present in the kidney or ureter can advance to the ureteral orifice device. In some cases, both the advanced urinary calculus and ureteral orifice device can freely pass into the bladder.

Even if a urinary calculus does not freely pass or advance following implantation of a ureteral orifice device provided herein, the implantation of such a device can prepare the mammal (e.g., human) for a later invasive or non-invasive stone removal procedure. For example, implanting a ureteral orifice device as described herein can lead to gradual ambulatory dilation and/or decreased inflammation, both of which allow for a more effective stone removal procedure. The previously implanted ureteral orifice device also can assist a clinician in locating and accessing the ureteral orifice during a stone removal procedure. Due to the preparatory effect of the proposed ureteral orifice device, the use of other adjunctive supplies (e.g., ureteral balloon dilators, ureteral access sheaths, and/or ureteral stents) for the actual definitive stone procedure may be minimized, thereby reducing overall procedural costs.

Ureteral orifice devices provided herein can be used to permit ureteral drainage and/or to facilitate healing after a definitive stone procedure. The safe gradual dilation and preparation achieved as described herein can occur with multiple benefits for the patients. For example, placement of a ureteral orifice device provided herein can occur as an office-based procedure and can be lower cost than stent placement under anesthesia. Additional cost savings can be realized when a ureteral orifice device provided herein permits spontaneous stone passage. For larger stones that are not ideal candidates for spontaneous passage, placement of a ureteral orifice device provided herein can occur days ahead of a definitive stone procedure with a beneficial effect of dilating that ureteral and reducing inflammation in the ureter. Both effects can help reduce the need for additional disposables in the operating room and need for additional operating room time. In some cases, use of a ureteral orifice device provided herein after a definitive stone procedure can facilitate drainage and reduce inflammation. In comparison to conventional techniques for urinary drainage, a ureteral orifice device provided herein can spontaneously pass, thereby eliminating an outpatient procedure to retrieve the device. In some cases, the preparation of the orifice using a ureteral orifice device provided herein can occur in a gradual fashion and can take place after the ureteral orifice device is placed in the ureteral orifice. In addition, the effects can be achieved on an ambulatory basis.

In general, one aspect of this document features a ureteral orifice device comprising, or consisting essentially of, a distal portion and a proximal portion and defining a channel that extends along a longitudinal axis of the ureteral orifice device, wherein at least an outer portion of the distal portion is configured to extend laterally away from the longitudinal axis to engage an inner wall of a ureter when the ureteral orifice device is implanted within a mammal, and wherein the channel is configured to allow urine to flow in an impeded manner through the ureteral orifice device from a kidney of the mammal to a bladder of the mammal when the ureteral orifice device is implanted within the mammal. The mammal can be a human. At least a portion of the proximal portion can extend into the bladder when the ureteral orifice device is implanted within the mammal. The proximal portion can comprise a flexible tail portion. The distal portion can comprise expandable material. The distal portion can comprise flexible material. The proximal portion can comprise an actuator configured to extend the outer portion of the distal portion laterally away from the longitudinal axis to engage the inner wall of the ureter when the ureteral orifice device is implanted within the mammal. The proximal portion, the distal portion, or both the proximal portion and the distal portion can comprise one or more physical or radiopaque markers. The length of the ureteral orifice device can be from about 2.5 cm to about 4.0 cm. The length of the distal portion can be from about 1.5 cm to about 2.0 cm. The length of the proximal portion can be from about 1.0 cm to about 2.0 cm. The outer diameter of the channel can be from about 5 French to 7 French. From about 20 percent to about 50 percent of the flow of the urine to the bladder can be impeded when the when the ureteral orifice device is implanted within the mammal. The ureteral orifice device can comprise an anti-inflammatory agent, a smooth muscle relaxing agent, or analgesic agents.

In another aspect, this document features a system comprising, or consisting essentially of, a ureteral orifice device and a deployment device. The ureteral orifice device can comprise, or consist essentially of, a distal portion and a proximal portion and defining a channel that extends along a longitudinal axis of the ureteral orifice device, wherein at least an outer portion of the distal portion is configured to extend laterally away from the longitudinal axis to engage an inner wall of a ureter when the ureteral orifice device is implanted within a mammal, and wherein the channel is configured to allow urine to flow in an impeded manner through the ureteral orifice device from a kidney of the mammal to a bladder of the mammal when the ureteral orifice device is implanted within the mammal. The mammal can be a human. At least a portion of the proximal portion can extend into the bladder when the ureteral orifice device is implanted within the mammal. The proximal portion can comprise a flexible tail portion. The distal portion can comprise expandable material. The distal portion can comprise flexible material. The proximal portion can comprise an actuator configured to extend the outer portion of the distal portion laterally away from the longitudinal axis to engage the inner wall of the ureter when the ureteral orifice device is implanted within the mammal. The proximal portion, the distal portion, or both the proximal portion and the distal portion can comprise one or more physical or radiopaque markers. The length of the ureteral orifice device can be from about 2.5 cm to about 4.0 cm. The length of the distal portion can be from about 1.5 cm to about 2.0 cm. The length of the proximal portion can be from about 1.0 cm to about 2.0 cm. The outer diameter of the channel can be from about 5 French to 7 French. From about 20 percent to about 50 percent of the flow of the urine to the bladder can be impeded when the when the ureteral orifice device is implanted within the mammal. The ureteral orifice device can comprise an anti-inflammatory agent, a smooth muscle relaxing agent, or analgesic agents. The deployment device can comprise a scope, a pusher element extending away from the scope, and an inner stylet located within the pusher element, wherein the inner stylet is configured to extent into the channel of the ureteral orifice device. The pusher element can be configured to contact a The ureteral orifice device and the deployment device can be connected via the inner stylet. The outer diameter of the inner stylet can be from about 2 mm to about 3 mm.

In another aspect, this document features a method for treating a mammal having a urinary calculus. The method comprises, or consists essentially of, implanting a ureteral orifice device into a ureteral orifice of the mammal, wherein at least a portion of the ureteral orifice device is located within about 1 cm to about 3 cm of the entrance of the ureteral orifice, wherein the ureteral orifice device comprises a distal portion and a proximal portion and defines a channel that extends along a longitudinal axis of the ureteral orifice device, wherein at least an outer portion of the distal portion engages an inner wall of a ureter of the mammal, and wherein the channel allows urine to flow in an impeded manner through the ureteral orifice device from a kidney of the mammal to a bladder of the mammal. The mammal can be a human. The urinary calculus can be a kidney stone. The ureteral orifice device can comprise, or consist essentially of, a distal portion and a proximal portion and defining a channel that extends along a longitudinal axis of the ureteral orifice device, wherein at least an outer portion of the distal portion is configured to extend laterally away from the longitudinal axis to engage an inner wall of a ureter when the ureteral orifice device is implanted within a mammal, and wherein the channel is configured to allow urine to flow in an impeded manner through the ureteral orifice device from a kidney of the mammal to a bladder of the mammal when the ureteral orifice device is implanted within the mammal. The mammal can be a human. At least a portion of the proximal portion can extend into the bladder when the ureteral orifice device is implanted within the mammal. The proximal portion can comprise a flexible tail portion. The distal portion can comprise expandable material. The distal portion can comprise flexible material. The proximal portion can comprise an actuator configured to extend the outer portion of the distal portion laterally away from the longitudinal axis to engage the inner wall of the ureter when the ureteral orifice device is implanted within the mammal. The proximal portion, the distal portion, or both the proximal portion and the distal portion can comprise one or more physical or radiopaque markers. The length of the ureteral orifice device can be from about 2.5 cm to about 4.0 cm. The length of the distal portion can be from about 1.5 cm to about 2.0 cm. The length of the proximal portion can be from about 1.0 cm to about 2.0 cm. The outer diameter of the channel can be from about 5 French to 7 French. From about 20 percent to about 50 percent of the flow of the urine to the bladder can be impeded when the when the ureteral orifice device is implanted within the mammal. The ureteral orifice device can comprise an anti-inflammatory agent, a smooth muscle relaxing agent, or analgesic agents. At least a portion of the proximal portion extends into the bladder. The ureter of the mammal can dilate following the implanting step. Inflammation within the ureter can be reduced following the implanting step. The urinary calculus can advance toward the ureteral orifice device following the implanting step. The urinary calculus and the ureteral orifice device can be spontaneously released into the bladder following the implanting step.

In another aspect, this document features a method for preparing a mammal having a urinary calculus for treatment. The method comprises implanting a ureteral orifice device into a ureteral orifice of the mammal, wherein at least a portion of the ureteral orifice device is located within about 1 cm to about 3 cm of the entrance of the ureteral orifice, wherein the ureteral orifice device comprises a distal portion and a proximal portion and defines a channel that extends along a longitudinal axis of the ureteral orifice device, wherein at least an outer portion of the distal portion engages an inner wall of a ureter of the mammal, and wherein the channel allows urine to flow in an impeded manner through the ureteral orifice device from a kidney of the mammal to a bladder of the mammal. The mammal can be a human. The urinary calculus can be a kidney stone. The ureteral orifice device can comprise, or consist essentially of, a distal portion and a proximal portion and defining a channel that extends along a longitudinal axis of the ureteral orifice device, wherein at least an outer portion of the distal portion is configured to extend laterally away from the longitudinal axis to engage an inner wall of a ureter when the ureteral orifice device is implanted within a mammal, and wherein the channel is configured to allow urine to flow in an impeded manner through the ureteral orifice device from a kidney of the mammal to a bladder of the mammal when the ureteral orifice device is implanted within the mammal. The mammal can be a human. At least a portion of the proximal portion can extend into the bladder when the ureteral orifice device is implanted within the mammal. The proximal portion can comprise a flexible tail portion. The distal portion can comprise expandable material. The distal portion can comprise flexible material. The proximal portion can comprise an actuator configured to extend the outer portion of the distal portion laterally away from the longitudinal axis to engage the inner wall of the ureter when the ureteral orifice device is implanted within the mammal. The proximal portion, the distal portion, or both the proximal portion and the distal portion can comprise one or more physical or radiopaque markers. The length of the ureteral orifice device can be from about 2.5 cm to about 4.0 cm. The length of the distal portion can be from about 1.5 cm to about 2.0 cm. The length of the proximal portion can be from about 1.0 cm to about 2.0 cm. The outer diameter of the channel can be from about 5 French to 7 French. From about 20 percent to about 50 percent of the flow of the urine to the bladder can be impeded when the when the ureteral orifice device is implanted within the mammal. The ureteral orifice device can comprise an anti-inflammatory agent, a smooth muscle relaxing agent, or analgesic agents. At least a portion of the proximal portion can extend into the bladder. The ureter of the mammal can dilate following the implanting step. Inflammation within the ureter can be reduced following the implanting step. The urinary calculus can advance toward the ureteral orifice device following the implanting step. The urinary calculus and the ureteral orifice device may not be spontaneously released into the bladder following the implanting step. The method can further comprise removing the ureteral orifice device from the mammal. A forceps element can be used to remove the ureteral orifice device from the mammal. The method can further comprise removing the urinary calculus from the mammal. A cystoscopic, ureteroscopic, nephroscopic or shockwave lithotripsy procedure can be performed to remove the urinary calculus from the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 2 is a diagram of a ureteral orifice device according to some embodiments. The ureteral orifice device is shown in the expanded state.

FIGS. 4A-D are diagrams of ureteral orifice devices with different luminal contact zone mechanisms according to some embodiments.

FIG. 6 is a diagram of a ureteral orifice device according to some embodiments. The ureteral orifice device is shown in the unexpanded state.

Like reference numbers represent corresponding parts throughout.

DETAILED DESCRIPTION

Figure 1:
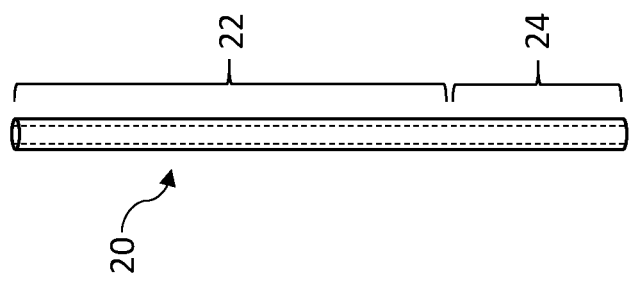
FIG. 1 is a diagram of a ureteral orifice device according to some embodiments. The ureteral orifice device is shown in the unexpanded state.

It is established that ureteral stones in the urinary tract and especially the ureter can create a number of pathophysiologic effects. A general concept is that the ureter dilates in the portion above the stone and that waves of ureteral peristalsis are increased. A second concept is that stones that present or migrate to the distal ureter have a higher chance of spontaneous passage. For example, stones with a diameter of about 4 mm in the distal ureter have a greater than 80 percent passage rate, whereas the same stone presenting in the proximal ureter typically has a spontaneous stone passage rate less than about 50 percent. A third concept is that the ureteral lumen can become progressively smaller in diameter as the ureter gets close to the bladder. For example, the normal ureteral diameter at the location where the ureter meets the bladder (at the ureteral orifice) of a human can be about 1 mm. In addition to location of the stone within the ureter, another factor that can influence spontaneous stone passage is stone size. For example, stones with diameters less than 1 mm can routinely pass. If the normal pathophysiologic responses to the stone do not create the right conditions in the ureter, the stone does not pass and may become surrounded by dense inflammation.

The methods and materials (e.g., ureteral orifice devices) provided herein can be used to augment ureter and/or ureteral orifice dilation, which can make spontaneous stone passage more successful and can better prepare the ureter (e.g., reduce peristalsis and/or reduce inflammation) for definitive stone treatment if required. They may also be used to continue to provide a benefit to the ureter following definitive stone treatments.

In some cases, placement of the ureteral orifice devices provided herein can occur during an office based outpatient cystoscopy with the patient awake. Using the deployment method and tools provided herein, the ureteral orifice devices can be placed into the ipsilateral ureteral orifice under direct visualization. In some cases, no fluoroscopy is required. The procedure can be performed in less than 5 minutes (e.g., less than 3 minutes) and can be accomplished with either a flexible or rigid endoscope. After placement, a brief observation period can be used to assure anatomic placement. In some cases, a cystoscopy can be completed, and a gradual ambulatory effect of the device can be realized. In some cases, a ureteral orifice device provided herein can be contraindicated for those stones that are already located in the far distal ureter and especially for those stones that are already at the ureteral orifice. A ureteral orifice device provided herein also can be contraindicated for patients presenting with urinary tract infection or with other significant comorbidity where ambulatory dilation of the ureter would be problematic.

The ureteral orifice devices provided herein can have financial benefits as fewer patients will need any further intervention (i.e., spontaneous passage rates can be higher and time to pass a stone can be shorter). In some cases, patients that need definitive stone treatment can have a shorter operative time since the ureter has been prepared using the methods and materials provided herein.

To place a ureteral orifice device provided herein, a specialized deployment tool and process can be used. With a flexible cystoscope, the deployment tool can be placed through the working channel of the cystoscope and then a ureteral orifice device can be back-loaded onto the deployment tool. In some cases, a ureteral orifice device can be placed directly through the working channel of the flexible cystoscope, instead of back-loading. In some cases, a ureteral orifice device provided herein can be place at the ureteral orifice such that at least a portion of the device that engages an inner surface of a ureter is within one to three centimeters of the opening face of the ureteral orifice. In some cases, a ureteral orifice device provided herein can be placed further within a ureter but not beyond the intended luminal contact zone. To facilitate correct anatomic placement the ureteral preparation device would be fashioned with markers that are visualized by direct visualization and also by other physical means (e.g., radiographic markers). During implantation of the ureteral orifice device, the deployment tool, which includes a cystoscope, can be placed into the bladder, the ureteral orifice can be identified, and the ureteral orifice device can be deployed under direct visualization.

In general, a ureteral orifice device can include three components: a center shaft, a luminal contact zone, and a manipulation zone. The luminal contact zone can be part of the distal portion of the ureteral orifice device, and the manipulation zone can be part of the proximal portion of the ureteral orifice device. For deployment and retrieval of the ureteral orifice device, contact can be made with the manipulation zone. During deployment with a flexible or rigid cystoscope or ureteroscope, graduations present on the ureteral orifice device can allow positioning of the luminal contact zone at the level of the ureteral orifice. Once the luminal contact zone interacts with the ureter, the ureteral preparation can begin. The dilation aspect of a ureteral orifice device provided herein can start shortly after deployment.

In some cases, using a rigid cystoscope, the technique for placement can include passing the cystoscope under direct vision into the bladder. At this point, a telescope and bride can be removed, and the deployment device can be inserted through a working channel. Then, a ureteral orifice device can be back-loaded onto the deployment device and held in place via, for example, friction. The telescope and bridge can then be replaced, and a ureteral orifice identified.

In some cases, hydroscopic dilation methods can be used with plant-based materials that are adherent to the luminal contact zone. For example, plant-based materials can be attached to the luminal contact zone such that those materials expand once the ureteral orifice device is implanted. This expansion can result in the ureteral orifice device becoming lodged within the ureter. Examples of such plant-based materials that can be used as described herein include, without limitation, Algue Brune, Brown Algae, Brown Seaweed, Hai Dai, Kelp, Kombu, Kun Bu, Laminaire, Laminaire Digitée, Laminaire Japonaise, Laminaria digitata, Laminaria japonica, Laminariae stipites, Limu, Makombu Thallus, Sea Girdles, Seagirdle Thallus, and Thallus Laminariae. These plant-based materials can be placed in a variety of configurations. For example, the plant-based materials can be configured to create a wedge effect at the ureteral orifice with the largest diameter located at the ureteral orifice. The wedge effect can facilitate the ureteral orifice device to be lodged within the ureter but also in the correct anatomical position to assure that the device spontaneously passes once the ureter is adequately prepared to facilitate stone passage or definitive stone procedure. In some cases, a wedge design can put more weight proximally (on the bladder lumen side) to assist with dilation and/or the expulsive process.

In some cases, components of the manipulation zone can reduce the chance the ureteral orifice device becomes lodged. From the manipulation zone, a tail element can be included to give more weight and downward pull on the luminal contact zone to facilitate a dilation process. In some cases, a tail element can be a suture or polymer material in a variety of configurations.

In some cases, other mechanisms can be used in place of expandable plant-based materials. For example, spring based mechanisms, memory coils, inflatable balloons, self-expanding foams, self-expanding polymers, and sponge materials can be used to create a luminal contact zone that can engage an inner surface of a ureter.

As gradual dilation commences, urinary drainage can be maintained via a channel defined, for example, through the center shaft or along a longitudinal axis of the ureteral orifice device. In some cases, a ureteral orifice device provided herein (e.g., a luminal contact zone of a ureteral orifice device) can include one or more regions that contain anti-inflammatory substances, smooth muscle relaxants, other medications (e.g., analgesics), or combinations thereof that can be used to promote decreased inflammation and relaxation of the ureter and analgesia.

In some cases, an intended effect of a ureteral orifice device provided herein is that the ureter dilates to permit a stone located in a more proximal position to migrate distally and ultimately pass. To achieve stone passage, ureteral dilation can occur with a ureteral orifice device provided herein to a point such that the device itself passes from the ureteral orifice followed by the stone. The process of dilation can occur during normal ambulatory effort by the mammal (e.g., human). In some cases, a ureteral orifice device may not cause spontaneous stone passage. In these situations, a ureteral orifice device provided herein can offer beneficial effects by starting the dilation process and relaxing the smooth muscle. In this manner, the disposable resource use and overall operating time can be reduced when the patient ultimately has a definitive stone procedure. In this context, there may be a need to remove the ureteral orifice device before the definitive stone procedure is performed. In these cases, a ureteral orifice device can be removed using a purpose-built grasping tools.

In some cases, a ureteral orifice device provided herein can be used after ureteroscopy or other definitive stone procedures (e.g. shockwave lithotripsy) to help provide drainage and likewise decrease inflammation seen after a ureteral manipulation.

In some cases, a ureteral orifice device provided herein can be considered part of a class of devices distinct from stents for multiple reasons. For example, stents are designed to relieve obstruction, while in some cases a ureteral orifice device provided herein can be designed to create obstruction. In particular, by creating a partial obstruction, a resultant pathophysiologic ureteral response can occur (e.g., increased ureteral peristalsis and/or increased ureteral dilation of the entire ureter, which can permit passage of the index stone that is above the implantation site).

With reference to FIGS. 1 and 2, a ureteral orifice device (20) can include a distal portion (22) and a proximal portion (24). Distal portion (22) can be configured to be in an unexpanded state prior to being implanted into a ureter orifice as depicted in FIG. 1 and can be configured to be in an expanded state after being implanted into a ureter orifice as depicted in FIG. 2. Distal portion (22) can include luminal contact zone (22a) designed to contact an inner surface of a ureter. In some cases, proximal portion (24) can include a manipulation zone (24a) designed to allow positioning and removal of the device. Proximal portion (24) can be designed to extend from a ureter orifice into a bladder. Ureteral orifice device (20) can define a channel (26; not shown in FIG. 1) that can extend along a longitudinal axis of the device. This channel can be configured to allow urine to flow from a kidney to the bladder through the device when the device is implanted at a ureteral orifice. This channel can be of diameter in some embodiments that facilitates a process of ureteral access whereby a guidewire can be place through the channel prior to device removal. In some cases, implanting ureteral orifice device (20) into a ureteral orifice as described herein can partially impede urine flow about 20 to about 50 percent of its pre-implantation urine flow rate. Without being limited to any particular mode of action, partially reducing urine flow rates and presence of the ureteral orifice device alone (e.g., foreign body) with resultant ureteral hyperperistalsis can promote dilation of a ureter.

Figure 3D:
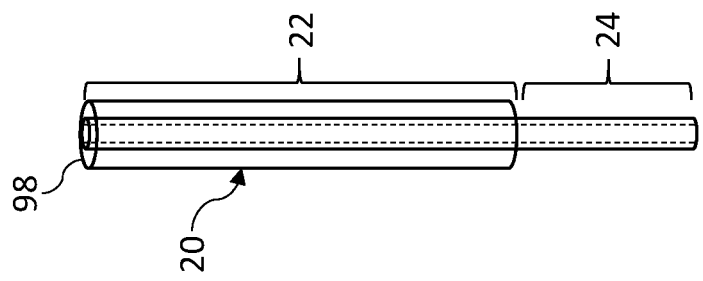
FIGS. 3A-D are diagrams of ureteral orifice devices with different luminal contact zone patterns according to some embodiments.
Figure 3C:
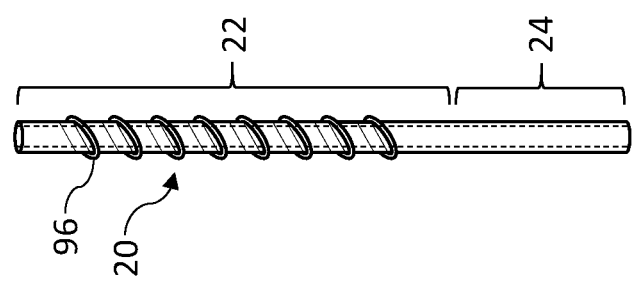
Figure 3B:
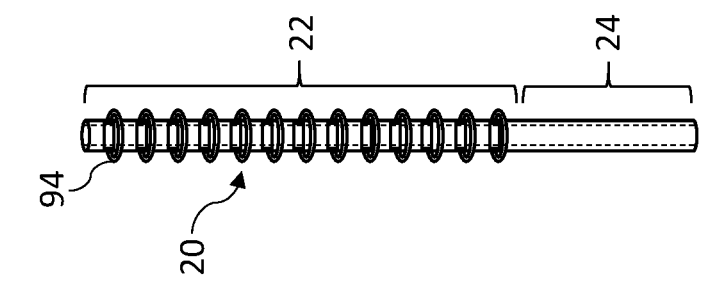
Figure 3A:
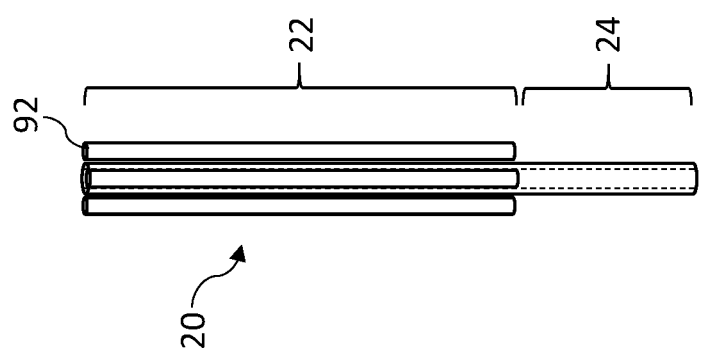
Figure 5B:
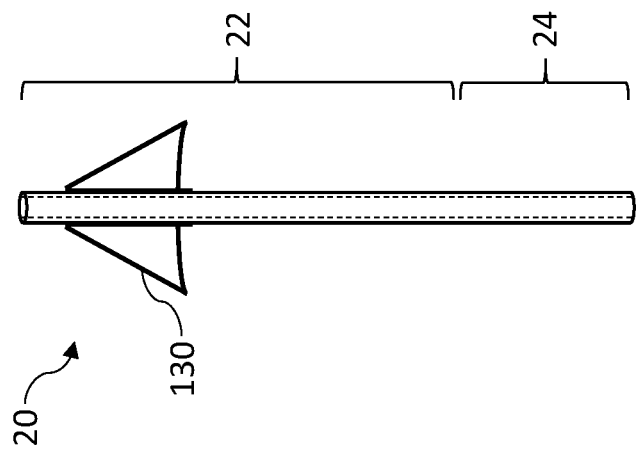
FIGS. 5A-B are diagrams of a ureteral orifice device in an unexpanded (FIG. 5A) and expanded (FIG. 5B) state according to some embodiments.
Figure 5A:
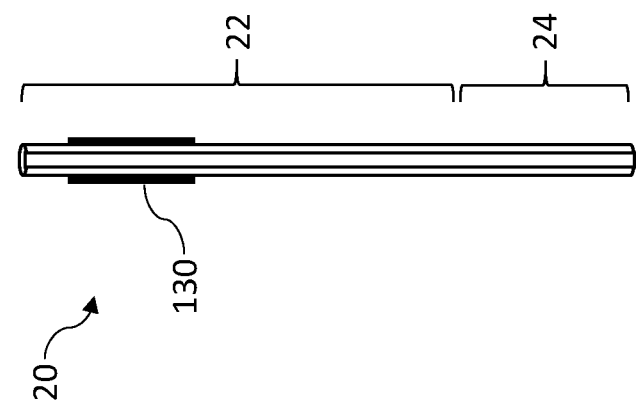

With further reference to FIG. 2, distal portion (22) can include an expandable portion that expands to any appropriate shape or can be pre-formed in any shape or can be deployed in a way to create a shape during the deployment process. For example, an expanded state of distal portion (22) can form a wedge shape similar to that depicted in FIG. 2. In some cases, distal portion (22) can include bar-shaped expandable elements (92; see FIG. 3A), rib-shaped expandable elements (94; see FIG. 3B), thread-shaped expandable elements (96; see FIG. 3C), and/or cross-hatched expandable elements (98; see FIG. 3D). In addition, distal portion (22) can include any appropriate type of mechanism for expanding so that luminal contact zone (22a) expands to a point where it contacts an inner surface of a ureter and remains in place in some embodiments. For example, expandable plant-based materials, spring-based mechanisms, memory coils, inflatable balloons, self-expanding foams, self-expanding polymers, and/or sponge materials can be used to create a ureteral orifice device that can expand into a position to hold it in place within a ureter. With reference to FIGS. 4A-D, distal portion (22) can include spring elements (102; see FIG. 4A), self-expanding polymers (104; see FIG. 4B), a balloon element (106) and port (107; see FIG. 4C), and/or memory coil elements (108; see FIG. 4D) to expand a portion of distal portion (22) to contact an inner surface of a ureter and retain the device in place. In some cases, as shown in FIGS. 5A and 5B, distal portion (22) can be configured to have in expandable cone element or funnel type element (130).

With reference to FIG. 6, in some cases, ureteral orifice device (20) can include a tail element (27) that extends from any location of proximal portion (24). Tail element (27) can be a flexible material such as polymer, synthetic fabric, or metallic source and can provide a clinician with a handle for retrieving the device. In some cases, distal portion (22) of ureteral orifice device (20) can include one or more radiopaque markers and/or markers that can be visualized endoscopically (28). Likewise, in some cases, proximal portion (24) of ureteral orifice device (20) can include one or more radiopaque markers (29). Radiopaque markers (28 and 29) can allow a clinician to use radiographic or fluoroscopic images to visualize the location of ureteral orifice device (20) within a mammal (e.g., a human). In this means, there is a mechanism to track the location of the device during the time of deployment.

Figure 7:
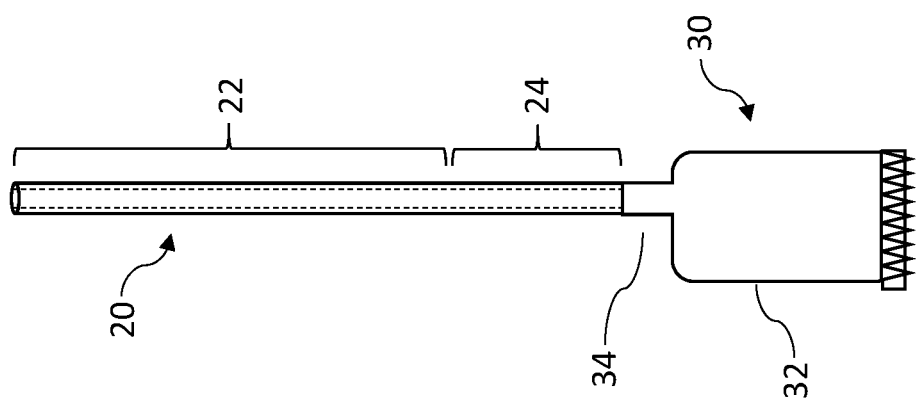
FIG. 7 is a diagram of a ureteral orifice device connected to a detachable deployment device according to some embodiments. The ureteral orifice device is shown in the unexpanded state.
Figure 8:
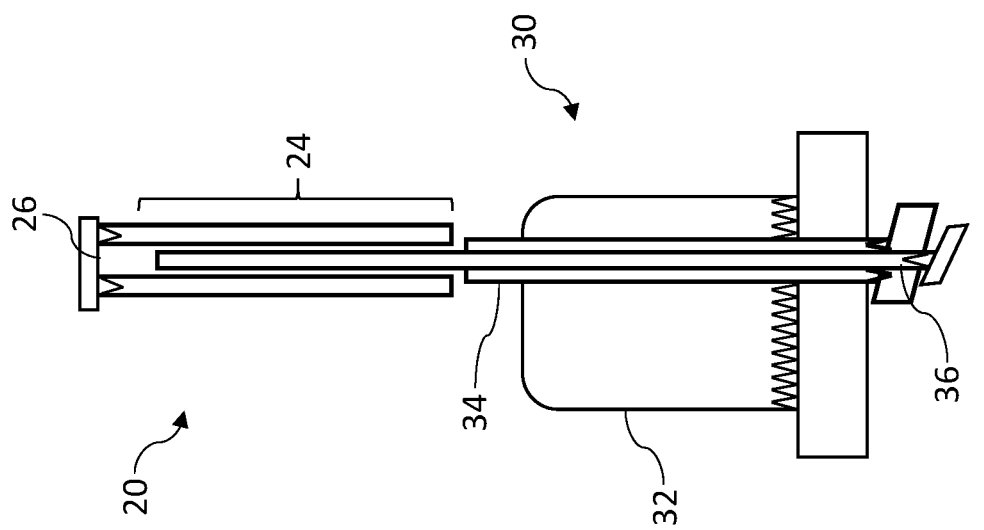
FIG. 8 is an enlarged diagram of an exemplary attachment configuration for connecting a ureteral orifice device to a detachable deployment device according to some embodiments.

Any appropriate medical tool (purpose-built or non-purpose-built) can be used to implant a ureteral orifice device into a ureteral orifice of a mammal (e.g., a human). For example, with reference to FIG. 7, deployment device (30) can be used to implant ureteral orifice device (20) into a mammal (e.g., a human). Deployment device (30) can include a cystoscope (32) and a pusher element (34). With reference to FIG. 8, pusher element (34) of deployment device (30) can movably extend away from and retract into a housing of cystoscope (32). In some cases, pusher element (34) can be configured to be fixed in place with respect to cystoscope (32). Pusher element (34) can define a channel for a stylet (36), which can slide within the channel to movably extend away from and retract into pusher element (34). Stylet (36) can be configured to fit within channel (26) of ureteral orifice device (20). When stylet (36) is positioned within channel (26), stylet (36) can hold ureteral orifice device (20) in place during implantation. When ureteral orifice device (20) is positioned into the proper position within a ureteral orifice, stylet (36) can be withdrawn from channel (26) to release ureteral orifice device (20) from deployment device (30).

Figure 9:
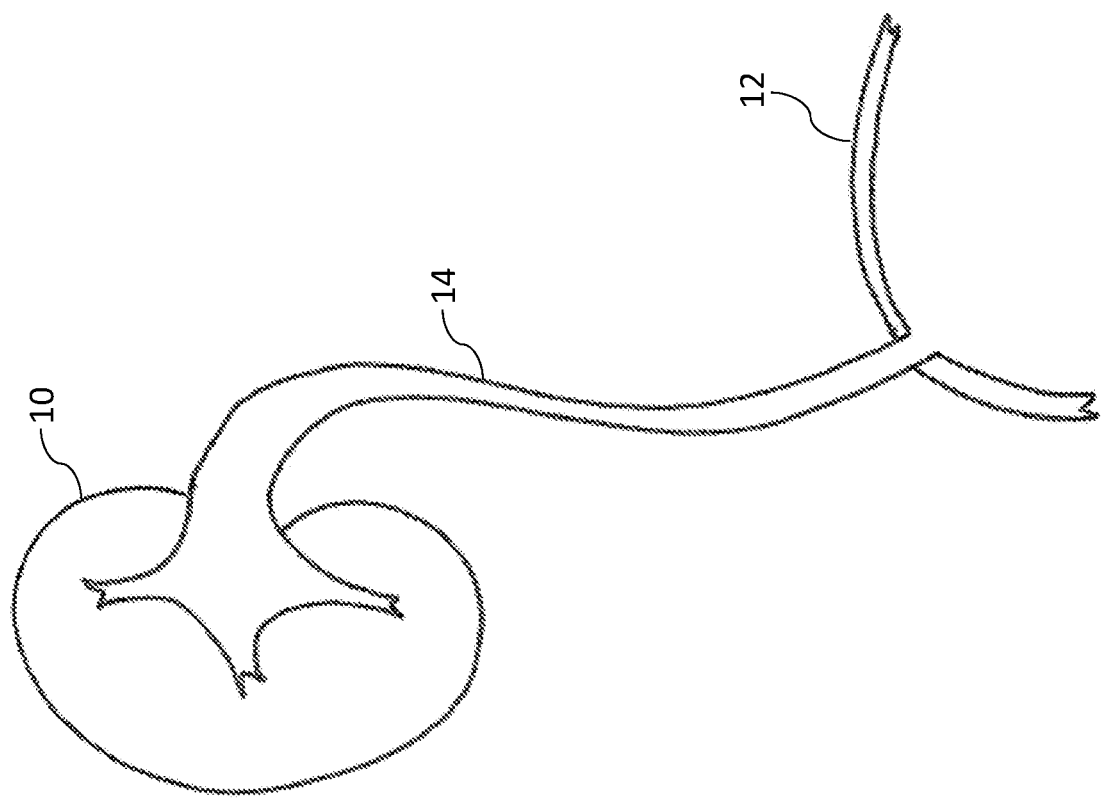
FIG. 9 is a schematic diagram of the anatomy of a kidney, ureter, and bladder. At the level of the intramural tunnel, the diameter of the ureter is about 1 mm in the normal state.
Figure 10:
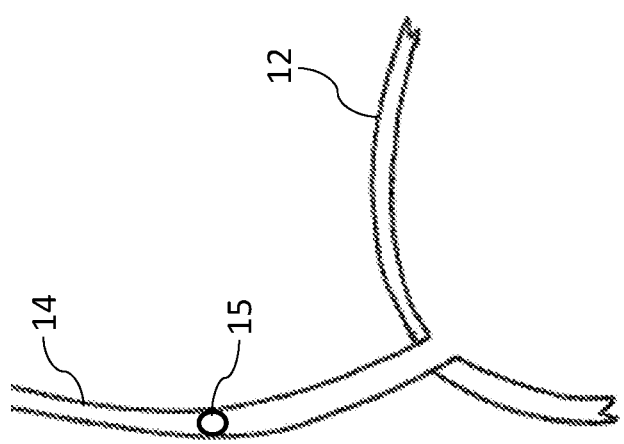
FIG. 10 is a schematic diagram of the anatomy of a ureter and bladder with a urinary calculus located in the ureter.
Figure 11:
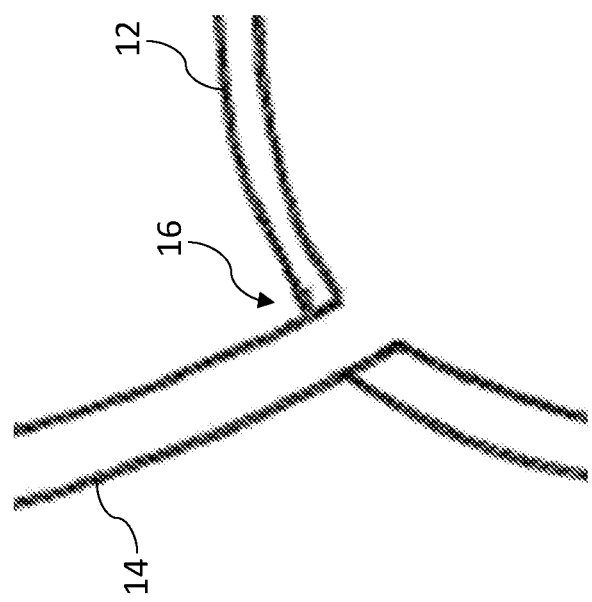
FIG. 11 is a schematic diagram of a ureteral orifice.
Figure 12C:
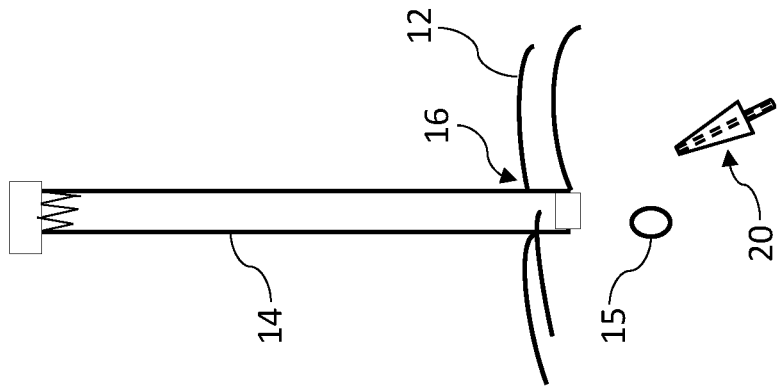
FIGS. 12A-C are diagrams of an implanted ureteral orifice device according to some embodiments during use within a mammal.
Figure 12B:
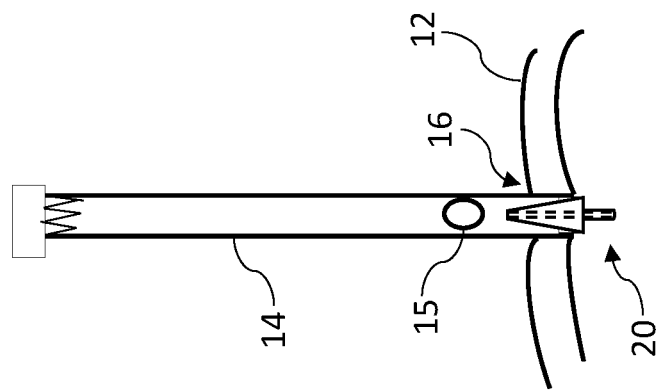
Figure 12A:
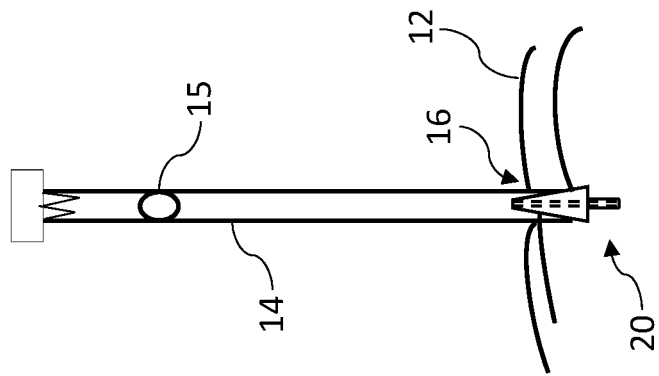
Figure 13:
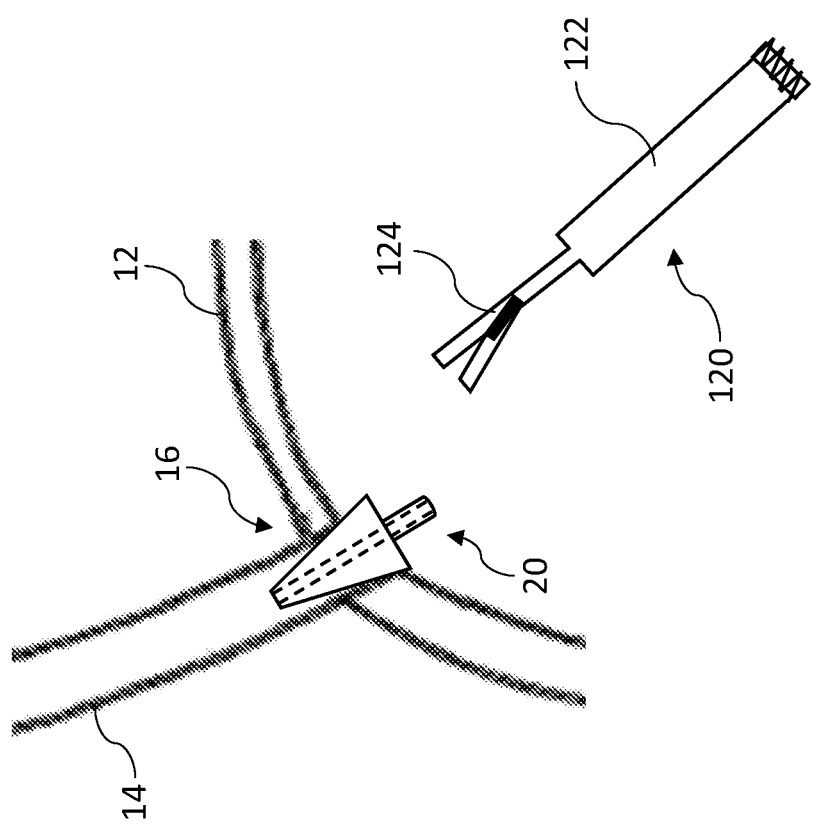
FIG. 13 is a diagram of a ureteral orifice device according to some embodiments being withdrawn from a mammal.

As described herein, a ureteral orifice device can be implanted into a ureteral orifice of a mammal (e.g., a human). With reference to FIG. 9, a kidney (10) is connected to a bladder (12) via ureter (14). Sometimes, ureter (14) can be become blocked or partially blocked with a urinary calculus (15) as shown in FIG. 10. FIG. 11 depicts an enlarged view of a ureteral orifice (16). As shown in FIGS. 12A-C, ureteral orifice device (20) can be implanted into ureteral orifice (16) with a urinary calculus (15) located within ureter (14) (FIG. 12A). After implanting ureteral orifice device (20), ureter (14) can dilate, and urinary calculus (15) can advance along ureter (14) toward ureteral orifice device (20) (FIG. 12B). In some cases, with additional dilation of ureter (14), both ureteral orifice device (20) and urinary calculus (15) can spontaneously pass into the bladder (FIG. 12C). In those cases where ureteral orifice device (20) does not spontaneously pass into the bladder, ureteral orifice device (20) can be manually removed, and another stone removal procedure can be performed as described herein. Any appropriate medical tool can be used to remove a ureteral orifice device from a ureteral orifice of a mammal (e.g., a human). For example, with reference to FIG. 13, grasping device (120) can be used to retrieve ureteral orifice device (20) from a mammal (e.g., a human). Grasping device (120) can include a cystoscope (122) and a grasper element (124).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. In addition, while the devices and concepts are being described for the ureteral orifice, the devices and concepts are applicable to any lumen whereby a need exists for instrumentation and/or spontaneous passage of a given material. For example, endoscopic placement of a similar device into the cystic duct can facilitate the spontaneous passage of gallstones. In addition, the devices and concepts being described also are applicable to preparation any orifice within mammals.

What is claimed is:

1. A ureteral orifice device comprising a distal portion and a proximal portion and defining a channel that extends along a longitudinal axis of said ureteral orifice device, wherein the length of said ureteral orifice device is from about 2.5 cm to about 4.0 cm, wherein at least a portion of said proximal portion extends into said bladder when said ureteral orifice device is implanted within said mammal, wherein at least an outer portion of said distal portion is configured to extend laterally away from said longitudinal axis to engage an inner wall of a ureter when said ureteral orifice device is implanted within a mammal, and wherein said channel is configured to allow urine to flow in an impeded manner through said ureteral orifice device from a kidney of said mammal to a bladder of said mammal when said ureteral orifice device is implanted within said mammal.

2. The ureteral orifice device of claim 1, wherein at least a portion of said proximal portion extends into said bladder when said ureteral orifice device is implanted within said mammal.

3. The ureteral orifice device of claim 1, wherein said proximal portion comprises an actuator configured to extend said outer portion of said distal portion laterally away from said longitudinal axis to engage said inner wall of said ureter when said ureteral orifice device is implanted within said mammal.

4. The ureteral orifice device of claim 1, wherein said proximal portion, said distal portion, or both said proximal portion and said distal portion comprise one or more physical or radiopaque markers.

5. The ureteral orifice device of claim 1, wherein said ureteral orifice device comprises an anti-inflammatory agent, a smooth muscle relaxing agent, or analgesic agents.

6. A method for treating a mammal having a urinary calculus, wherein said method comprises implanting a ureteral orifice device into a ureteral orifice of said mammal, wherein at least a portion of said ureteral orifice device is located within about 1 cm to about 3 cm of the entrance of said ureteral orifice, wherein said ureteral orifice device comprises a distal portion and a proximal portion and defines a channel that extends along a longitudinal axis of said ureteral orifice device, wherein the length of said ureteral orifice device is from about 2.5 cm to about 4.0 cm, wherein at least a portion of said proximal portion extends into said bladder, wherein at least an outer portion of said distal portion engages an inner wall of a ureter of said mammal, and wherein said channel allows urine to flow in an impeded manner through said ureteral orifice device from a kidney of said mammal to a bladder of said mammal.

7. The method of claim 6, wherein at least a portion of said proximal portion extends into said bladder.

8. The method of claim 6, wherein said ureter of said mammal dilates following said implanting step.

9. The method of claim 6, wherein inflammation within said ureter is reduced following said implanting step.

10. The method of claim 6, wherein said urinary calculus advances toward said ureteral orifice device following said implanting step.

11. The method of claim 6, wherein said urinary calculus and said ureteral orifice device are spontaneously released into said bladder following said implanting step.

12. A method for preparing a mammal having a urinary calculus for treatment, wherein said method comprises implanting a ureteral orifice device into a ureteral orifice of said mammal, wherein at least a portion of said ureteral orifice device is located within about 1 cm to about 3 cm of the entrance of said ureteral orifice, wherein said ureteral orifice device comprises a distal portion and a proximal portion and defines a channel that extends along a longitudinal axis of said ureteral orifice device, wherein the length of said ureteral orifice device is from about 2.5 cm to about 4.0 cm, wherein at least a portion of said proximal portion extends into said bladder, wherein at least an outer portion of said distal portion engages an inner wall of a ureter of said mammal, and wherein said channel allows urine to flow in an impeded manner through said ureteral orifice device from a kidney of said mammal to a bladder of said mammal.

13. The method of claim 12, wherein said ureter of said mammal dilates following said implanting step.

14. The method of claim 12, wherein inflammation within said ureter is reduced following said implanting step.

15. The method of claim 12, wherein said urinary calculus advances toward said ureteral orifice device following said implanting step.

16. The method of claim 12, wherein said urinary calculus and said ureteral orifice device are not spontaneously released into said bladder following said implanting step.

17. The method of claim 16, wherein said method further comprises removing said ureteral orifice device from said mammal.

18. The method of claim 17, wherein a forceps element is used to remove said ureteral orifice device from said mammal.

19. The method of claim 17, wherein said method further comprises removing said urinary calculus from said mammal.

20. The method of claim 19, wherein a cystoscopic, ureteroscopic, nephroscopic or shockwave lithotripsy procedure is performed to remove said urinary calculus from said mammal.

* * * * *